United States Patent [19]
Brown et al.

[11] Patent Number: 5,085,741
[45] Date of Patent: Feb. 4, 1992

[54] EXTRACTIVE DISTILLATION OF LOW BOILING ALKENE/ALKANE MIXTURES

[75] Inventors: Ronald E. Brown; Anthony L. Rouse; Fu-Ming Lee, all of Bartlesville, Okla.

[73] Assignee: Phillips Petroleum Company, Bartlesville, Okla.

[21] Appl. No.: 644,782

[22] Filed: Jan. 23, 1991

[51] Int. Cl.⁵ .............................................. B01D 3/40
[52] U.S. Cl. ......................................... 203/53; 203/14; 203/68; 203/95; 208/313; 208/337; 585/867
[58] Field of Search ........................ 203/14, 95, 53, 68, 203/98; 208/337, 313; 585/800, 809, 833, 867

[56] References Cited

U.S. PATENT DOCUMENTS

| | | | |
|---|---|---|---|
| 3,242,642 | 3/1966 | Miller et al. | 55/44 |
| 3,401,112 | 9/1968 | Dunlop et al. | 208/308 |
| 3,617,535 | 11/1971 | Weitz et al. | 208/326 |
| 3,769,217 | 10/1973 | Bannister et al. | 203/53 |
| 4,695,672 | 9/1987 | Bunting | 585/867 |
| 4,740,222 | 4/1988 | Mehra | 62/17 |

OTHER PUBLICATIONS

"Extractive Distillation Saves Energy" by Ian Sucksmith, Chemical Engineering, Jun. 28, 1982, pp. 91-95.
"Perry's Chemical Engineers' Handbook", Sixth Edition, pp. 13-53 to 13-57.
"Handbook of Separation Techniques for Chemical Engineers", by Philip A. Schweitze, 1979, pp. 1-135 to 1-143.

*Primary Examiner*—Virginia Manoharan
*Attorney, Agent, or Firm*—K. K. Brandes

[57] ABSTRACT

An extractive distillation process for separating at least one $C_2$-$C_4$ alkene (preferably propylene) from at least one close-boiling alkane (preferably propane) employs propylene carbonate as solvent, optionally in admixture with a minor amount of water.

16 Claims, 1 Drawing Sheet

EXTRACTIVE DISTILLATION OF LOW BOILING ALKENE/ALKANE MIXTURES

BACKGROUND OF THE INVENTION

This invention relates to the separation of low molecular weight alkenes (monoolefins) from close-boiling alkanes (paraffins) by extractive distillation.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, June 28, 1982, pages 91–95. Other literature sources on extractive distillation techniques include the *Handbook of Separation Techniques for Chemical Engineers* by Phillip A. Schweitzer, McGraw-Hill Book Company, 1979, pages 1-135 to 1-143; and Perry's Chemical Engineers Handbook, 6th Edition, McGraw-Hill Book Company 1984, pages 13-53 to 13-57.

SUMMARY OF THE INVENTION

It is an object of this invention to provide a process for separating $C_2$-$C_4$ alkenes from close-boiling alkanes by extractive distillation employing a selective solvent (also referred to as extractant or entrainer). Other objects and advantages will be apparent from the detailed description of the invention and the appended claims.

In accordance with this invention, a process for separating at least one alkene containing 2-4 carbon atoms per molecule (preferably propylene) from at least one close-boiling alkane (preferably propane) by extractive distillation of a feed comprising (preferably consisting essentially of) said at least one alkene and said at least one close-boiling alkane employs a solvent consisting essentially of propylene carbonate, optionally admixed with water.

DETAILED DESCRIPTION OF THE INVENTION

Figure 1:
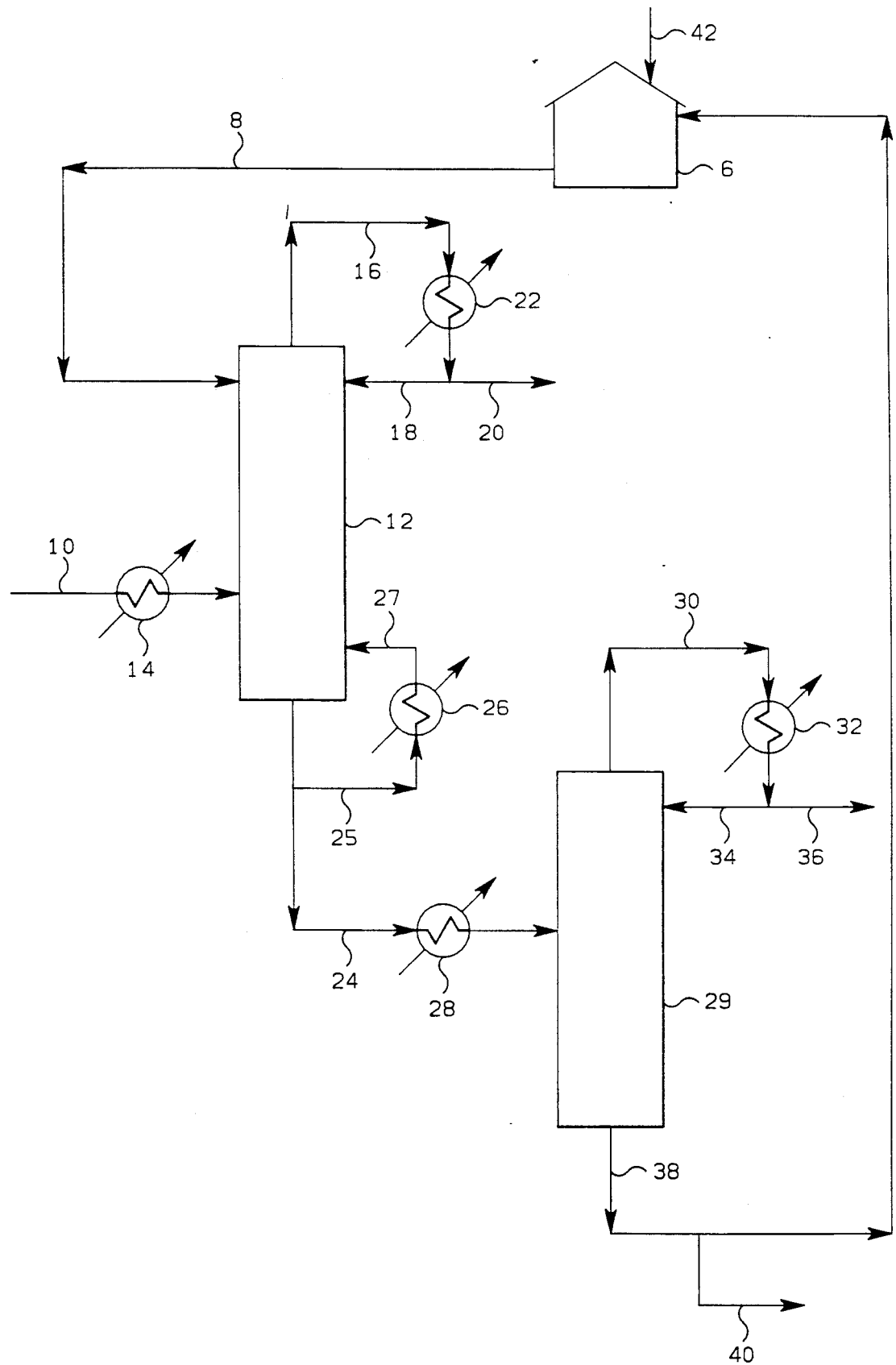
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity. The term "close-boiling" as used herein, means that the alkene(s) and the alkane(s) contained in the feed have nearly the same boiling point at atmospheric presssure.

In the process of this invention, any hydrocarbon feed which contains at least one alkene containing 2-4 carbon atoms per molecule and at least one close-boiling alkane (preferably containing 2-4 carbon atoms per molecule) can be used in the extractive distillation process of this invention. Preferably, the boiling points, measured at about 135 psig, of the alkene(s) and of the alkane(s) to be separated by the extractive distillation process of this invention, are in the range of from about −60° to about 190° F., about 135 psig, of the alkene(s) and of the alkane(s) differ by about 0.2-15° F. (preferably about 1°-13° F.).

Preferably, the monoolefin (alkene) content in the feed is about 10-95 weight-% (more preferably about 20-80 weight-%), and the alkane content is about 5-90 weight-% (more preferably about 20-80 weight-%).

Examples of suitable feed alkanes are ethane, propane, and isobutane. Examples of suitable alkenes are ethylene, propylene and 2-methylpropene (isobutene), and mixtures thereof; in particular propylene.

The general structural formula of propylene carbonate which are useful as the solvent in the process of this invention is

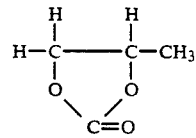

In one preferred embodiment, the solvent used in the process of this invention consists essentially of a mixture of (a) propylene carbonate as major component and (b) water as a minor component. Preferably the solvent contains about 1-10 weight-% $H_2O$. It is within the scope of this invention, (yet presently not preferred) to employ an alcohol, such as cyclohexanol, or a glycol compound, such as tetraethylene glycol, or a glycol ether, such as the monobutyl ether of diethylene glycol (also referred to a butyl carbitol), as cosolvent (b), either in lieu of or in addition to water. Cuprous salts should be essentially absent from the solvent.

Any suitable weight ratio of the solvent to the hydrocarbon containing feed mixture can be employed. Preferably, the solvent to feed weight ratio is in the range of from about 0.5:1 to about 40:1, more preferably from about 5:1 to about 15:1.

Any suitable reflux ratio (i.e., the weight ratio of the portion of condensed vapor which is returned to the distillation column to the portion of condensed vapor which is withdrawn as distillate product) can be employed in the extractive distillation process of this invention. Generally the reflux ratio is in the range of from about 0.1:1 to about 100:1, preferably in the range of from about 0.5:1 to about 50:1, more preferably in the range of from about 1:1 to about 20:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 100° about 500° F., preferably in the range of from about 250° to about 400° C. The extractive distillation column is generally heated (more near the bottom, and less near the top). Generally, the temperature at the top of the column where the vapor exits into the condenser is in the range of from about 80° to about 140° F., preferably in the range of from about 100° to about 130° F. Solvent and feed are generally preheated (generally to a temperature close to the column temperature of the corresponding entry point) before they are introduced into the column. Any suitable pressure can be employed during the extractive distillation. Generally the pressure is about 80 to about 300 psig, preferably about 110 to about 275 psig.

The overhead product (withdrawn from the top of the column) generally contains a smaller volume percentage of the alkene(s) than the feed and a larger volume percentage of alkane(s) than the feed. Generally, the bottoms product (a portion of which can be reheated and recycled to the lower portion of the column) contains more of the alkene(s) than the feed, and less of the alkane(s) than the feed. Furthermore, the bottoms product contains essentially all of the added solvent, which can be separated from the other bottoms product components by distillation or other suitable separating means and then be recycled to the extractive distillation column.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the various product, and the like, and can be determined by those having ordinary skills in the art.

The invention can be better understood by reference to FIG. 1 and the following description of a preferred embodiment of the invention. The feed mixture comprising alkene(s) and close-boiling alkane(s) is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in alkane(s) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in alkane(s) and a bottoms stream predominantly comprising the alkene(s) and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising alkene(s) is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., alkene(s) of high purity (preferably higher than 95%), through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The following example is presented to further illustrate the invention and is not to be considered unduly limiting the scope of this invention.

EXAMPLE

This example demonstrates the use of propylene carbonate as solvent in the extractive distillation of a propylene/propane feed.

To a hydrocarbon mixture of 50 weight-% propylene and 50 weight-% propane, under a pressure of about 140 psig, was added an extractive solvent (either propylene carbonate alone or in admixture with 1–10 weight- % H₂O) at various solvent:feed weight ratios. The total mixture (including the extractive solvent) was heated in a constant temperature bath to about 75° F., and the vapor was circulated in a Jurgenson cell for about 20-30 minutes until equilibrium conditions were attained (i.e., until a constant pressure was obtained). Then a small sample was withdrawn by means of a sample bomb from the flask containing the liquid phase of the equilibrium system, and a sample of the vapor was withdrawn by means of a sample bomb located just above the cell. Both samples were analyzed, and the mole fractions of propane and propylene in the liquid phase and in the vapor phase were determined by means of a gas chromatograph. The relative volatility R was calculated as follows:

$$R = \frac{Y1/Y2}{X1/X2} = \frac{Y1/X1}{Y2/X2},$$

wherein Y1 and Y2 are the mole fractions of and propane and propylene, respectively, in the vapor phase; and X1 and X2 are the mole fractions of propane and propylene, respectively, in the liquid phase. Test results are summarized in Table I.

TABLE I

| Solvent:Feed Weight Ratio | Added Solvent | Relative Volatility R |
|---|---|---|
| 7:1 | PC¹ alone² | 1.39 |
| 7:1 | PC + 1 wt % H₂O² | 1.35 |
| 7:1 | PC + 2 wt % H₂O² | 1.44 |
| 7:1 | PC + 5 wt % H₂O² | 1.49 |
| 7:1 | PC + 10 wt % H₂O² | 1.50 |
| 10:1 | PC alone | 1.62 |
| 10:1 | PC + 1 wt % H₂O² | 1.60 |
| 10:1 | PC + 2 wt % H₂O | 1.66 |
| 10:1 | PC + 5 wt % H₂O² | 1.73 |
| 10:1 | PC + 10 wt % H₂O² | 1.72 |

¹propylene carbonate
²two liquid phases were present

Based on the test results in Table I, it is concluded that propylene carbonate, preferably containing about 2–10 weight-% water, is an effective solvent in the extractive distillation of feeds containing C₂–C₄ alkene(s) and close-boiling alkane(s).

Reasonable variations, modifications and adaptations for various usages and conditions can be made within the scope of the disclosure and the appended claims, without departing from the scope of this invention.

That which is claimed is:

1. A process for separating propylene from propane by extractive distillation of a feed consisting essentially of propylene and propane, said process employing a solvent which consists essentially of propylene carbonate;
   wherein cuprous salts are essentially absent from said solvent; wherein said process produces (i) an overhead product which contains a smaller volume percentage of propylene and a larger volume percentage of propane than said feed, and (ii) a bottoms product which contains said solvent and a larger volume percentage of propylene and a smaller volume percentage of propane than said feed; and wherein propylene is separated from said solvent and recovered from said bottoms product.

2. A process in accordance with claim 1, wherein the weight ratio of said solvent to said feed is in the range of from about 0.5:1 to about 40:1.

3. A process in accordance with claim 2 wherein said weight ratio is in the range of from about 1:1 to about 10:1.

4. A process in accordance with claim 1, wherein said feed consists essentially of about 10-95 weight-% propylene and about 5-90 weight-% propane.

5. A process for separating propylene from propane by extractive distillation of a feed consisting essentially of propylene and propane, said process employing a solvent consisting essentially of a mixture of propylene carbonate and about 2-10 weight-% water;
   wherein cuprous salts are essentially absent from said solvent; wherein said extractive distillation process produces (i) an overhead product which contains a smaller volume percentage of propylene and a larger volume percentage of propane than said feed, and (ii) a bottoms product which contains said solvent and a larger volume percentage of propylene and a smaller volume percentage of propane than said feed; and wherein propylene is separated from said solvent and recovered from said bottoms product.

6. A process in accordance with claim 5, wherein the weight ratio of said solvent to said feed is in the range of from about 0.5:1 to about 40:1.

7. A process in accordance with claim 9, wherein said weight ratio is in the range of from about 1:1 to about 10:1.

8. A process in accordance with claim 5, wherein said feed consists essentially of about 10-95 weight-% propylene and about 5-90 weight-% propane.

9. A process for separating at least one alkene containing from 2 to 4 carbon atoms per molecule from at least one close-boiling alkane by extractive distillation of a feed consisting essentially of said at least one alkene and said at least one alkane, said process employing a solvent consisting essentially of propylene carbonate;
   wherein cuprous salts are essentially absent from said solvent; wherein said extractive distillation process produces (i) an overhead product which contains a smaller volume percentage of said at least one alkene and a larger volume percentage of said at least one alkane than said feed, and (ii) a bottoms product which contains said solvent and a larger volume percentage of said at least one alkene and a smaller volume percentage of said at least one alkane than said feed; and wherein said at least one alkene is separated from said solvent and recovered from said bottoms product.

10. A process in accordance with claim 9, wherein said at least one alkene is selected from the group consisting of ethylene, propylene and isobutylene.

11. A process in accordance with claim 9, wherein said at least one alkane is selected from the group consisting of ethane, propane and isobutane.

12. A process in accordance with claim 9, wherein said feed consists essentially of about 10-95 weight-% of said at least one alkene and about 5-90 weight-% of said at least one alkane.

13. A process in accordance with claim 9, wherein said feed boils at a temperature in the range of from about −60° F. to about 190° F., measured at a pressure of about 135 psig.

14. A process in accordance with claim 9, wherein the boiling point of said at least one alkene and the boiling point of said at least one alkane differ about 0.2°-15° F., meaured at a pressure of about 135 psig.

15. A process in accordance with claim 9, wherein the weight ratio of said solvent to said feed is in the range of from about 0.5:1 to about 40:1.

16. A process in accordance with claim 15, wherein said weight ratio is in the range of from about 1:1 to about 10:1.

* * * * *